United States Patent
Van Holten et al.

(10) Patent No.: US 8,299,316 B2
(45) Date of Patent: Oct. 30, 2012

(54) HEMOSTATIC DEVICE

(75) Inventors: Robert W. Van Holten, Flemington, NJ (US); Jagdishchandra C. Patel, Lawrenceville, NJ (US); Stephen C. Yeadon, Hampton, NJ (US)

(73) Assignee: Ethicon, Inc., Somerville, NJ (US)

( * ) Notice: Subject to any disclaimer, the term of this patent is extended or adjusted under 35 U.S.C. 154(b) by 324 days.

(21) Appl. No.: 11/958,796

(22) Filed: Dec. 18, 2007

(65) Prior Publication Data

US 2009/0156711 A1 Jun. 18, 2009

(51) Int. Cl.
*A61F 13/00* (2006.01)
*A61L 24/00* (2006.01)

(52) U.S. Cl. ............... 602/44; 523/118; 602/45; 602/48
(58) Field of Classification Search .................... 523/118
See application file for complete search history.

(56) References Cited

U.S. PATENT DOCUMENTS

| | | |
|---|---|---|
| 3,364,200 A | 1/1968 | Ashton et al. |
| 4,581,324 A | 4/1986 | Wolff et al. |
| 4,626,253 A | 12/1986 | Broadnax, Jr. |
| 4,900,554 A | 2/1990 | Yanagibashi et al. |
| 5,002,551 A | 3/1991 | Linsky et al. |
| 5,007,916 A | 4/1991 | Linsky et al. |
| 5,180,398 A | 1/1993 | Boardman et al. |
| 5,851,579 A | 12/1998 | Wu et al. |
| 5,900,245 A | 5/1999 | Sawhney et al. |
| 6,051,248 A | 4/2000 | Sawhney et al. |
| 6,162,241 A | 12/2000 | Coury et al. |
| 6,217,894 B1 | 4/2001 | Sawhney et al. |
| 6,323,278 B2 | 11/2001 | Rhee et al. |
| 6,352,710 B2 | 3/2002 | Sawhney et al. |
| 6,410,645 B1 | 6/2002 | Pathak et al. |
| 6,458,889 B1 | 10/2002 | Trollsas et al. |
| 6,495,127 B1 | 12/2002 | Wallace et al. |
| 6,534,591 B2 | 3/2003 | Rhee et al. |
| 6,541,460 B2 | 4/2003 | Petito |
| 6,624,245 B2 | 9/2003 | Wallace et al. |
| 6,733,774 B2 | 5/2004 | Stimmeder |
| 6,762,336 B1 | 7/2004 | MacPhee et al. |
| 6,833,408 B2 | 12/2004 | Sehl et al. |
| 6,911,496 B2 | 6/2005 | Rhee et al. |
| 6,969,400 B2 | 11/2005 | Rhee et al. |
| 7,198,786 B2 | 4/2007 | Redl et al. |
| 2004/0214770 A1* | 10/2004 | Reich et al. .............. 514/12 |
| 2004/0258723 A1 | 12/2004 | Singh et al. |
| 2005/0037055 A1 | 2/2005 | Yang et al. |
| 2005/0113849 A1 | 5/2005 | Popadiuk et al. |
| 2005/0226916 A1* | 10/2005 | Cochrum et al. .............. 424/445 |
| 2005/0271737 A1 | 12/2005 | Chinea et al. |
| 2006/0051340 A1 | 3/2006 | Uchida et al. |
| 2006/0147492 A1* | 7/2006 | Hunter et al. .............. 424/426 |
| 2006/0240064 A9* | 10/2006 | Hunter et al. .............. 424/423 |
| 2006/0258995 A1 | 11/2006 | Pendharkar et al. |
| 2008/0071300 A1 | 3/2008 | Popadiuk et al. |
| 2008/0206293 A1 | 8/2008 | Toreki et al. |

FOREIGN PATENT DOCUMENTS

| | | |
|---|---|---|
| EP | 1 424 086 A2 | 10/1984 |
| EP | 0 275 550 A1 | 7/1988 |
| EP | 0 815 881 A2 | 1/1998 |
| EP | 1 341 561 B1 | 2/2007 |
| GB | 2 393 655 A | 4/2004 |
| WO | 03/026544 A1 | 4/2003 |
| WO | 2004/024195 A1 | 3/2004 |
| WO | 2004/028547 A1 | 4/2004 |
| WO | WO 2004/064878 A1 | 8/2004 |
| WO | 2007/117237 A1 | 10/2007 |

OTHER PUBLICATIONS

N Jaji, "Laparoscopic Repair of Perforated Peptic Ulcers Versus Convention Open Surgery", Laparoscopic Hospital, New Delhi, India, Jul. 2007.
Graham, D.Y., "Treatment of Peptic Ulcers Caused by Helicobacter Pylori", 328 N. Engl J. Med, pp. 349-350 (1993).
A.J. Donovan, "Perforated Duodenal Ulcer an Alternative Therapeutic Plan", 133 Arch Surg. pp. 1166-1171 (Nov. 1998).
Vandamme, T. T"he Use of Polysaccharides to Target Drugs to the Colon", 48 Car Poly, pp. 219-231 (2002).
Herbert A. Lieberman and Leon Lachman, Pharmaceutical Dosage Forms: Tables vol. 3, Chapters 2, 3, and 4 (1982).
Encyclopedia of Polymer Science and Engineering, "Molecular Weight Determination to Pentadiene Polymers", vol. 10, pp. 204-253 (1987).
International Search Report of International Application No. PCT/US2008/087493 dated Mar. 22, 2010.
International Search Report of International Application No. PCT/US2008/087500 dated Apr. 15, 2010.

* cited by examiner

*Primary Examiner* — Peter F Godenschwager
*Assistant Examiner* — David Karst
(74) *Attorney, Agent, or Firm* — David R. Crichton

(57) ABSTRACT

A hemostatic device comprising (i) a carrier comprising at least one component selected from the group consisting of hydroxypropyl methylcellulose phthalate, hydroxypropyl methylcellulose acetate succinate, cellulose acetate phthalate; polyvinylacetate phthalate, cellulose acetate phthalate, acetaldehyde dimethylcellulose acetate, polymethacrylate-based polymers, and derivatives, salts, copolymers or combinations thereof; and (ii) thrombin.

42 Claims, No Drawings

HEMOSTATIC DEVICE

FIELD OF THE INVENTION

The present invention is directed to a hemostatic device comprising a two component reactive system in a delivery vehicle or carrier.

BACKGROUND OF THE INVENTION

The control of bleeding as well as sealing of air and various bodily fluids is essential and critical in surgical procedures to minimize blood loss, to seal tissue and organ structures, to reduce post-surgical complications, and to shorten the duration of the surgery in the operating room.

A two component reactive adhesive or sealant system comprised of components that can polymerize in situ to form an adhesive or sealant may be used to control such bleeding. For example, an adhesive or sealant system comprising one or more electrophilic moiety and one or more nucleophilic moiety may be prepared and delivered to a surgical site to control bleeding, or to seal tissue or organ structures. Examples of such adhesive or sealant systems are disclosed in U.S. Pat. No. 7,868,123, which is incorporated by reference thereto in its entirety. Additional examples of such adhesives include those described in U.S. Pat. Nos. 6,534,591, 6,410,645, 6,352,710, 6,217,894, 6,162,241, 6,051,248, 5,900,245, 6,969,400, 6,911,496, 6,833,408, 6,624,245, 6,495,127, 6,458,889 and 6,323,278, namely crosslinked polymer compositions that are the reaction product of a first synthetic polymer containing two or more nucleophilic groups and a second synthetic polymer containing two or more electrophilic groups capable of covalently binding with the nucleophilic groups on the first synthetic polymer. In addition to the synthetic adhesive and sealant systems described above, biologic components such as thrombin and fibrinogen have been used commercially to control bleeding. Due to the reactive nature of such two component reactive adhesive or sealant systems in the presence of moisture, the two reactive components are typically maintained separately and admixed in liquid form just prior to use in surgery to prevent premature polymerization of the components. However, one of the drawbacks associated with use of such two component reactive systems is the time required to prepare and admix the two reactive components to form the adhesive or sealant that is applied to the surgical site, and the fact that additional supplies are required to facilitate the admixing. Therefore, it is desirable to have a hemostatic device that does not require preparation and that is ready for use upon removal from its packaging.

Additionally, efforts have been made to provide dressings with enhanced hemostatic and tissue sealing and adhering properties. For example, thrombin and fibrinogen have been combined with dressing carriers or substrates, including gelatin-based carriers, polysaccharide-based carriers, glycolic acid or lactic acid-based carriers and a collagen matrix. Examples of such dressings are disclosed in U.S. Pat. Nos. 6,762,336, 6,733,774 and PCT publication WO 2004/064878 A1. Hemostatic wound dressings having one or more electrophilic moiety and one or more nucleophilic moiety disposed thereon in a dry state is also disclosed in co-pending U.S. application Ser. No. 11/942,035. Premature reaction of these two component reactive systems is avoided since the reactive components are maintained in a dry state on the dressing. However, one problem associated with using such components in dry form on a substrate is adherence of the dry components to the substrate. Therefore, it is desirable to have a hemostatic wound dressing having these two reactive components immobilized on the substrate to avoid loss of the components upon use.

SUMMARY OF THE INVENTION

The present invention is directed to a hemostatic device comprising a two component reactive system in a delivery vehicle or carrier.

DETAILED DESCRIPTION OF THE INVENTION

The device described herein provides and maintains effective hemostasis when applied to a wound requiring hemostasis. Effective hemostasis, as used herein, is the ability to control and/or abate capillary, venous, or arteriole bleeding within an effective time, as recognized by those skilled in the art of hemostasis. Further indications of effective hemostasis may be provided by governmental regulatory standards and the like.

In certain embodiments, the device of the present invention is effective in providing and maintaining hemostasis in cases of severe or brisk bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia.

As described above, the hemostatic device comprises at least two reactive components that are capable of polymerizing in situ to form an adhesive or sealant. In the case where it is desirable to have a hemostatic device comprised of synthetic moieties, the first reactive component may be an electrophilic moiety while the second reactive component may be a nucleophilic moiety. In the case where it is desirable to have a hemostatic device comprised of biologic components, the first reactive component may be thrombin while the second reactive component may be fibrinogen.

The delivery vehicle or carrier comprises at least one component selected from any one of the hydroxypropyl methylcellulose phthalate, hydroxypropyl methylcellulose acetate succinate, cellulose acetate phthalate; enteric acetate derivatives such as for example polyvinylacetate phthalate, cellulose acetate phthalate and acetaldehyde dimethylcellulose acetate; and enteric acrylate derivatives such as for example polymethacrylate-based polymers such as poly(methacrylic acid, methyl methacrylate) 1:2 (which is commercially available from Rohm Pharma GmbH under the tradename "EUDRAGIT S") and poly(methacrylic acid, methyl methacrylate) 1:1 (which is commercially available from Rohm Pharma GmbH under the tradename, "EUDRAGIT L"), and derivatives, salts, copolymers, and combinations thereof.

Optionally, the carrier may comprise additional components including but not limited to hydroxypropylcellulose, methylcellulose, hydroxypropylmethylcellulose, hydroxyethylmethylcellulose, hydroxyethylcellulose and hydroxyethylethylcellulose.

The delivery vehicle or carrier has a first and second face, and the two reactive components may be dispersed within the carrier or may be applied to one face of the carrier. Alternatively, one of the reactive components may be applied to the first face while the second reactive components may be applied to the second face; or one of the reactive components may be dispersed within the carrier and the other reactive component may be applied on one of the faces of the carrier.

The device may also comprise a nonwoven, woven or knitted fabric having the carrier coated thereon on one or both faces of the fabric. In addition to serving as a carrier for the two components, the coating shields the components from acidic moieties that may be present in the fabric, for example in the case where carboxylic-oxidized cellulose is used as the fabric.

The fabric may be comprised of oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used to prepare the second absorbable woven or knitted fabric. Regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents each of which is hereby incorporated by reference as if set forth in its entirety. Examples of fabrics that may be utilized include, but are not limited to, Interceed® absorbable adhesion barrier, Surgicel® absorbable hemostat; Surgicel Nu-Knit® absorbable hemostat; and Surgicel® Fibrillar absorbable hemostat; each available from Johnson & Johnson Wound Management Worldwide or Gynecare Worldwide, each a division of Ethicon, Inc., Somerville, N.J.

The fabric may optionally, or additionally, be comprised of fibers of aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Preferably, the fabric comprises a copolymer of glycolide and lactide, in an amount ranging from about 70 to 95% by molar basis of glycolide and the remainder lactide.

The fabric may be comprised of aliphatic polyester polymers, copolymers, or blends thereof alone or in combination with oxidized polysaccharide fibers.

The fabric may be made weaving or knitting or known methods for making non-wovens. The fabric utilized in the present invention may be woven or knitted, for example, as described in U.S. Pat. Nos. 4,626,253, 5,002,551 and 5,007,916, the contents of which are hereby incorporated by reference herein as if set forth in its entirety. For example, the fabric is a warp knitted tricot fabric constructed of bright rayon yarn that is subsequently oxidized to include carboxyl or aldehyde moieties in amounts effective to provide the fabrics with biodegradability.

A nonwoven fabric may be prepared from yarn, scrims, netting or filaments that have been made by processes that include, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be carded to create a nonwoven batt, which may be then needlepunched or calendared into a nonwoven fabric. Additionally, the staple may be kinked or piled.

Other methods known for the production of nonwoven fabrics may be utilized and include such processes as air laying, wet forming and stitch bonding. Such procedures are generally discussed in the Encyclopedia of Polymer Science and Engineering, Vol. 10, pp. 204-253 (1987) and Introduction to Nonwovens by Albin Turbank (Tappi Press, Atlanta Ga. 1999), both incorporated herein in their entirety by reference.

As used herein, the term "nonwoven fabric" includes, but is not limited to, bonded fabrics, formed fabrics, or engineered fabrics, that are manufactured by processes other than, weaving or knitting. More specifically, the term "nonwoven fabric" refers to a porous, textile-like material, usually in flat sheet form, composed primarily or entirely of staple fibers assembled in a web, sheet or batt. The structure of the nonwoven fabric is based on the arrangement of, for example, staple fibers that are typically arranged more or less randomly. The tensile, stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include, weaving or knitting.

The fabric may be coated on one or both of its faces with the carrier. As described above, both of the reactive components may be dispersed within the carrier or applied to the face of the carrier that is opposite the face that is contiguous to the fabric; or one of the reactive components may be dispersed within the carrier while the other reactive component may be applied to the face of the carrier opposite the face that is contiguous to the fabric.

Optionally, the device may have thereon an active component selected from the group consisting of albumin, ancrod, batroxobin, ecarin, elastin, epinephrine, Factor X/Xa, Factor VII/VIIa, Factor IX/IXa, Factor XI/XIa, Factor XII/XIIa, fibrin, ficolin, fibronectin, gelatin, globin, haptoglobin, hemoglobin, heparinase, inhibin, insulin, interleukin, lamininthrombin, platelet surface glycoproteins, prothrombin, selectin, transferin, von Willebrand Factor, vasopressin, vasopressin analogs, procoagulant venom, platelet activating agents and synthetic peptides having hemostatic activity. One or more of these active components may be used on the device in combination with the two reactive components.

The device described herein may be used as an adjunct to primary wound closure devices, such as arterial closure devices, staples, and sutures, to seal potential leaks of gasses, liquids, or solids as well as to provide hemostasis. For example, the device may be utilized to seal air from tissue or fluids from organs and tissues, including but not limited to, bile, lymph, cerebrospinal fluids, gastrointestinal fluids, interstitial fluids and urine.

The device described herein has additional medical applications and may be used for a variety of clinical functions, including but not limited to tissue reinforcement and buttressing, i.e., for gastrointestinal or vascular anastomoses, approximation, i.e., to connect anastomoses that are difficult to perform (i.e. under tension), and tension releasing. The device may additionally promote and possibly enhance the natural tissue healing process in all the above events. This device can be used internally in many types of surgery, including, but not limited to, cardiovascular, peripheral-vascular, cardio-thoracic, gynecological, neuro- and general surgery. The device may also be used to attach medical devices (e.g. meshes, clips and films) to tissues, tissue to tissue, or medical device to medical device.

EXAMPLE 1

0.2 grams of Cellulose acetate phthalate (CAP), 0.2 grams of hydroxylpropyl cellulose (HPC), 0.1 grams of glycerol, 4 ml of acetone and 6 ml of ethanol were added to a test tube and vortexed for approximately 5 minutes. The mixture was concentrated by passing dry air over its surface to remove the acetone and ethanol. Once the mixture had the consistency of cold honey, the mixture is applied and spread over the surface of a 2 sq. inch piece of Surgicel Nu-Knit® fabric. Thrombin powder of 20 IU/mg powder is distributed over the surface of the coating to a concentration of 50 IU/sq. cm. fabric.

EXAMPLE 2

An aortic injury was made by dissection of the infrarenal abdominal aorta of a swine, to obtain a 4 mm punch in the aorta. An approximately 1 sq. inch square of the device made in Example 1 was placed over the edge of the bleeding injury and direct pressure was applied with a tamponade for three minutes without moving or twisting the hemostatic device. Bleeding was stopped within three minutes and the device was secure affixed to the injury site, with a strong pulse being observed through the hemostatic device.

The Surgicel Nu-Knit® fabric may be removed to observe the wound, for example, by irrigating the area with sterile saline and teasing the fabric from the clot, without disturbing the clot and leaving a transparent film for inspection of the site of bleeding.

While the examples demonstrate certain embodiments of the invention, they are not to be interpreted as limiting the scope of the invention, but rather as contributing to a complete description of the invention.

We claim:

1. A hemostatic device consisting of a nonwoven, woven or knitted fabric substrate, and a hemostatic coating on one or both faces thereof comprising:
   a carrier selected from the group consisting of hydroxypropyl methylcellulose phthalate, hydroxypropyl methylcellulose acetate succinate, polyvinylacetate phthalate, cellulose acetate phthalate, acetaldehyde dimethylcellulose acetate, polymethacrylate-based polymers, and derivatives, salts, copolymers and combinations thereof; and
   at least two reactive components that are capable of polymerizing only in situ, which are fibrinogen and thrombin, where the fibrinogen is adjacent to a surface of the coating but not adjacent to the substrate, and the thrombin is adjacent to the substrate but not adjacent to the surface of the coating.

2. The hemostatic device of claim 1, where the carrier component is cellulose acetate phthalate.

3. The hemostatic device of claim 1, where the nonwoven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ε-caprolactone, p-dioxanone, and trimethylene carbonate.

4. The hemostatic device of claim 1, wherein the hemostatic coating further comprises an electrophilic component and a nucleophilic component.

5. The hemostatic device of claim 4, where the carrier component is cellulose acetate phthalate.

6. The hemostatic device of claim 5, where the nucleophilic component and electrophilic component are dispersed within the cellulose acetate phthalate carrier coating.

7. The hemostatic device of claim 5, where the nucleophilic component is adjacent to a surface of the coating while the electrophilic component is adjacent to the substrate.

8. The hemostatic device of claim 5, where the nucleophilic component is dispersed within the cellulose acetate phthalate carrier coating, and the electrophilic component, is adjacent to a surface of the coating.

9. The hemostatic device of claim 5, where the electrophilic component is dispersed within the cellulose acetate phthalate carrier coating, and the nucleophilic component is adjacent to a surface of the coating.

10. The hemostatic device of claim 4, where the nonwoven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ε-caprolactone, p-dioxanone, and trimethylene carbonate.

11. A hemostatic device consisting of a carrier sheet having first and second faces, selected from the group consisting of hydroxypropyl methylcellulose phthalate, hydroxypropyl methylcellulose acetate succinate, polyvinylacetate phthalate, cellulose acetate phthalate, acetaldehyde dimethylcellulose acetate, polymethacrylate-based polymers, and derivatives, salts, copolymers and combinations thereof, and at least two reactive components that are capable of polymerizing only in situ, which are fibrinogen and thrombin; and optionally a supporting substrate for said carrier sheet, where the fibrinogen is on the first face but not on the second face, and the thrombin is on the second face but not on the first face.

12. The hemostatic device of claim 11, wherein a nonwoven, woven or knitted fabric supporting substrate is present.

13. A hemostatic device consisting of a nonwoven, woven or knitted fabric substrate, and a hemostatic coating on one or both faces thereof comprising: a carrier selected from the group consisting of hydroxypropyl methylcellulose phthalate, hydroxypropyl methylcellulose acetate succinate, polyvinylacetate phthalate, cellulose acetate phthalate, acetaldehyde dimethylcellulose acetate, polymethacrylate-based polymers, and derivatives, salts, copolymers and combinations thereof; and at least two reactive components that are capable of polymerizing in situ, which are fibrinogen and thrombin, where the thrombin is adjacent to a surface of the coating but not adjacent to the substrate, and the fibrinogen is adjacent to the substrate but not adjacent to the surface of the coating.

14. The hemostatic device of claim 13, where the carrier component is cellulose acetate phthalate.

15. The hemostatic device of claim 5, where the nonwoven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ε-caprolactone, p-dioxanone, and trimethylene carbonate.

16. The hemostatic device of claim 13, wherein the hemostatic coating further comprises an electrophilic component and a nucleophilic component.

17. The hemostatic device of claim 16, where the carrier component is cellulose acetate phthalate.

18. The hemostatic device of claim 17, where the nucleophilic component and electrophilic component are dispersed within the cellulose acetate phthalate carrier coating.

19. The hemostatic device of claim 17, where the nucleophilic component is adjacent to a surface of the coating while the electrophilic component is adjacent to the substrate.

20. The hemostatic device of claim 17, where the nucleophilic component is dispersed within the cellulose acetate phthalate carrier coating, and the electrophilic component, is adjacent to a surface of the coating.

21. The hemostatic device of claim 17, where the electrophilic component is dispersed within the cellulose acetate phthalate carrier coating, and the nucleophilic component is adjacent to a surface of the coating.

22. The hemostatic device of claim 16, where the non-woven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ϵ-caprolactone, p-dioxanone, and trimethylene carbonate.

23. A hemostatic device consisting of a nonwoven, woven or knitted fabric substrate, and a hemostatic coating on one or both faces thereof comprising: a carrier selected from the group consisting of hydroxypropyl methylcellulose phthalate, hydroxypropyl methylcellulose acetate succinate, polyvinylacetate phthalate, cellulose acetate phthalate, acetaldehyde dimethylcellulose acetate, polymethacrylate-based polymers, and derivatives, salts, copolymers and combinations thereof; and at least two reactive components that are capable of polymerizing in situ, which are fibrinogen and thrombin, where the fibrinogen is dispersed within the carrier coating but not adjacent to a surface of the carrier coating, and the thrombin is adjacent to the surface of the coating but not dispersed within the carrier coating.

24. The hemostatic device of claim 23, where the carrier component is cellulose acetate phthalate.

25. The hemostatic device of claim 23, where the non-woven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ϵ-caprolactone, p-dioxanone, and trimethylene carbonate.

26. The hemostatic device of claim 23, wherein the hemostatic coating further comprises an electrophilic component and a nucleophilic component.

27. The hemostatic device of claim 26, where the carrier component is cellulose acetate phthalate.

28. The hemostatic device of claim 27, where the nucleophilic component and electrophilic component are dispersed within the cellulose acetate phthalate carrier coating.

29. The hemostatic device of claim 27, where the nucleophilic component is adjacent to a surface of the coating while the electrophilic component is adjacent to the substrate.

30. The hemostatic device of claim 27, where the nucleophilic component is dispersed within the cellulose acetate phthalate carrier coating, and the electrophilic component, is adjacent to a surface of the coating.

31. The hemostatic device of claim 27, where the electrophilic component is dispersed within the cellulose acetate phthalate carrier coating, and the nucleophilic component is adjacent to a surface of the coating.

32. The hemostatic device of claim 26, where the non-woven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ϵ-caprolactone, p-dioxanone, and trimethylene carbonate.

33. A hemostatic device consisting of a nonwoven, woven or knitted fabric substrate, and a hemostatic coating on one or both faces thereof comprising: a carrier selected from the group consisting of hydroxypropyl methylcellulose phthalate, hydroxypropyl methylcellulose acetate succinate, polyvinylacetate phthalate, cellulose acetate phthalate, acetaldehyde dimethylcellulose acetate, polymethacrylate-based polymers, and derivatives, salts, copolymers and combinations thereof; and at least two reactive components that are capable of polymerizing in situ, which are fibrinogen and thrombin, where the thrombin is dispersed within the carrier coating but not adjacent to a surface of the carrier coating, and the fibrinogen is adjacent to the surface of the coating but not dispersed within the carrier coating.

34. The hemostatic device of claim 33, where the carrier component is cellulose acetate phthalate.

35. The hemostatic device of claim 33, where the non-woven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ϵ-caprolactone, p-dioxanone, and trimethylene carbonate.

36. The hemostatic device of claim 33, wherein the hemostatic coating further comprises an electrophilic component and a nucleophilic component.

37. The hemostatic device of claim 36, where the carrier component is cellulose acetate phthalate.

38. The hemostatic device of claim 37, where the nucleophilic component and electrophilic component are dispersed within the cellulose acetate phthalate carrier coating.

39. The hemostatic device of claim 37, where the nucleophilic component is adjacent to a surface of the coating while the electrophilic component is adjacent to the substrate.

40. The hemostatic device of claim 37, where the nucleophilic component is dispersed within the cellulose acetate phthalate carrier coating, and the electrophilic component, is adjacent to a surface of the coating.

41. The hemostatic device of claim 37, where the electrophilic component is dispersed within the cellulose acetate phthalate carrier coating, and the nucleophilic component is adjacent to a surface of the coating.

42. The hemostatic device of claim 36, where the non-woven, woven or knitted fabric comprises fibers comprised of oxidized polysaccharides, aliphatic polyester polymers and/or copolymers of one or more monomers selected from the group consisting of lactic acid, L-lactide, D-lactide, meso-lactide, D,L-lactide mixtures, glycolic acid, glycolide, ϵ-caprolactone, p-dioxanone, and trimethylene carbonate.

* * * * *